United States Patent [19]

Fiala

[11] Patent Number: Plant 6,956

[45] Date of Patent: Aug. 1, 1989

[54] CRABAPPLE TREE NAMED SATIN CLOUD

[75] Inventor: John L. Fiala, Medina, Ohio

[73] Assignee: Chas. Klehm & Son, South Barrington, Ill.

[21] Appl. No.: 213,915

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Foley & Lardner, Schwartz, Jeffery, Schwaab Mack, Blumenthal & Evans

[57] ABSTRACT

An ornamental tetraploid flowering crabapple tree named Satin Cloud, having a ball-shaped, wide compact, billowy and rounded habit. Dark rose buds open to cinnamon fragrant satiny white blossoms with occasional pink tinging. Its waxy spring leaves are green with amber blushes, and the summer-long, disease resistant foliage is leathery and dark green. This low maintenance, closely internoded cultivar displays an autumn leaf color of burnt red, with gold leaves in the center shade part of the canopy.

4 Drawing Sheets

1

The present invention comprises a new and distinct cultivar of crabapple tree, botanically known as Malus, and hereinafter referred to by the cultivar name Satin Cloud.

The new cultivar, discovered by the inventor in 1969, resulted from a controlled cross by the inventor of seed parent (Malus 'Coralburst'×tetraploid *Malus zumi*) with pollen parent (tetraploid Malus 'Dorthea' seedling-×tetraploid *Malus zumi*) in Medina, Ohio. Asexual reproduction in the form of rooted cuttings and summer chip budding by the inventor in Medina, Ohio, has demonstrated that the combination of characteristics as herein disclosed for the new cultivar are firmly fixed and are retained through successive generations of asexual reproduction.

Satin Cloud has not been observed under all possible environmental conditions. The phenotype may vary significantly with variations in environment such as temperature, light intensity, day length, available soil moisture, soil nutrients and pH level.

The following observations, measurements and comparisons describe trees grown at Klehm Nursery, Barrington, Ill., under conditions which approximate those generally used in commercial practice.

The following traits have been repeatedly observed and are determined to be basic characteristics of Satin Cloud which, in combination, distinguish this crabapple tree as a new and distinct cultivar:

1. Satin Cloud is a ball-shaped tetraploid variety, with a compact, billowy and rounded habit.
2. It produces fragrant, cinnamon scented white blossoms. Its dark rose buds open to satiny white blossoms with white-pink highlights.
3. Its waxy, medium green spring leaves are overlaid with amber blushes. The leaves are leathery and disease resistant and turn to dark green in summer.
4. The cultivar produces excellent autumn leaf color; fiery red outer leaves with gold leaves in the center shade part of the canopy.
5. The cultivar requires little, if any, pruning or maintenance. Its fine branches are closely internoded.
6. Its fruit is small ($\frac{3}{8}$″), and amber to tannish yellow in color.

Of the many commercial crabapple trees known to the inventor, none is similar enough to Satin Cloud for meaningful comparison.

2

The accompanying photographic drawings show typical characteristics of Satin Cloud, with colors being as true as possible with illustrations of this type.

Sheet 1 is a photograph of Satin Cloud in perspective view.

Sheet 2 is a closeup photograph of a branch of Satin Cloud showing fully opened blossoms.

Sheet 3 is a closeup photograph of a fruit-bearing branch of Satin Cloud.

Sheet 4 is a perspective view of Satin Cloud with autumn foliage.

In the following detailed description, color references are made to The Royal Horticultural Society Colour Chart (R.H.S.).

TREE

Origin: Seedling.

Parentage:

*Seed parent.*—(Malus 'Coralburst'×tetraploid *Malus zumi*).

*Pollen parent.*—(Tetraploid Malus 'Dorthea' seedling×tetraploid *Malus zumi*).

Classification:

*Botanic.*—Malus×cv 'Satin Cloud'.

*Commercial.*—Ornamental flowering crabapple.

Propagation: Summer chip budding, bench grafting or softwood cuttings.

Branches: Fine textured, with close internodes.

Height: Ball shaped, approximately 12 feet by 12 feet at 15 years.

Growth habit: Roundish, ball-shaped, full and dense.

Fruit bearing habit: Annual, average amount.

Foliage:

*Size of leaf.*—Small, 1–1.5″ long by 0.5–0.75″ wide.

*Shape of leaf.*—Elliptical.

*Texture.*—Tight.

*Color.*—New spring leaves are waxy and medium green in color; autumn leaves are red around periphery and golden in shade part of canopy.

FLOWERS

Buds:

*Color.*—Dark rose.

*Shape.*—Round and clustered.

Form: Clustered.

Date of first bloom: Normally May 10–15.

Date of full bloom: Normally May 15–20.

Color: Mature blooms are satin white 155A, with occasional slight tinging of pinkish rose.

FRUIT

Date of maturity: October 15.

Shape: Round.

Hardness: Very firm and hard. Color: Amber to yellow-tan, 22A-B.

Insect and disease resistance: Highly resistant to common flowering crabapple diseases.

Primary use: Ornamental and landscaping.

I claim:

1. A new and unique flowering crabapple tree named Satin Cloud, as illustrated and described.

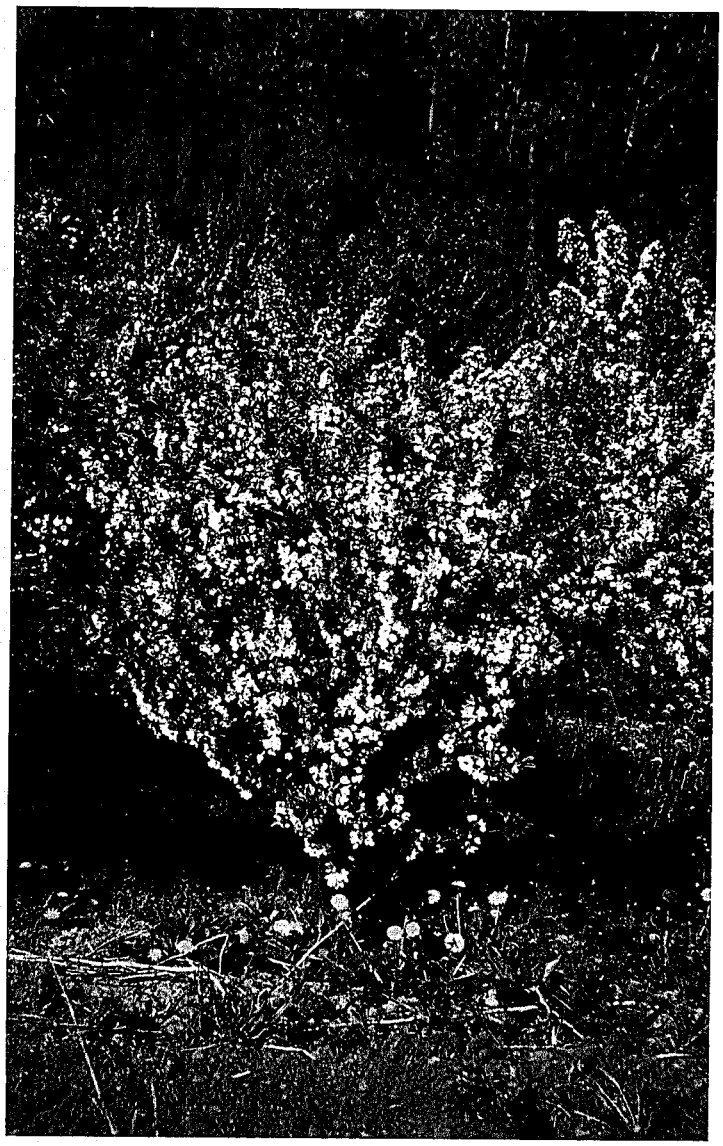

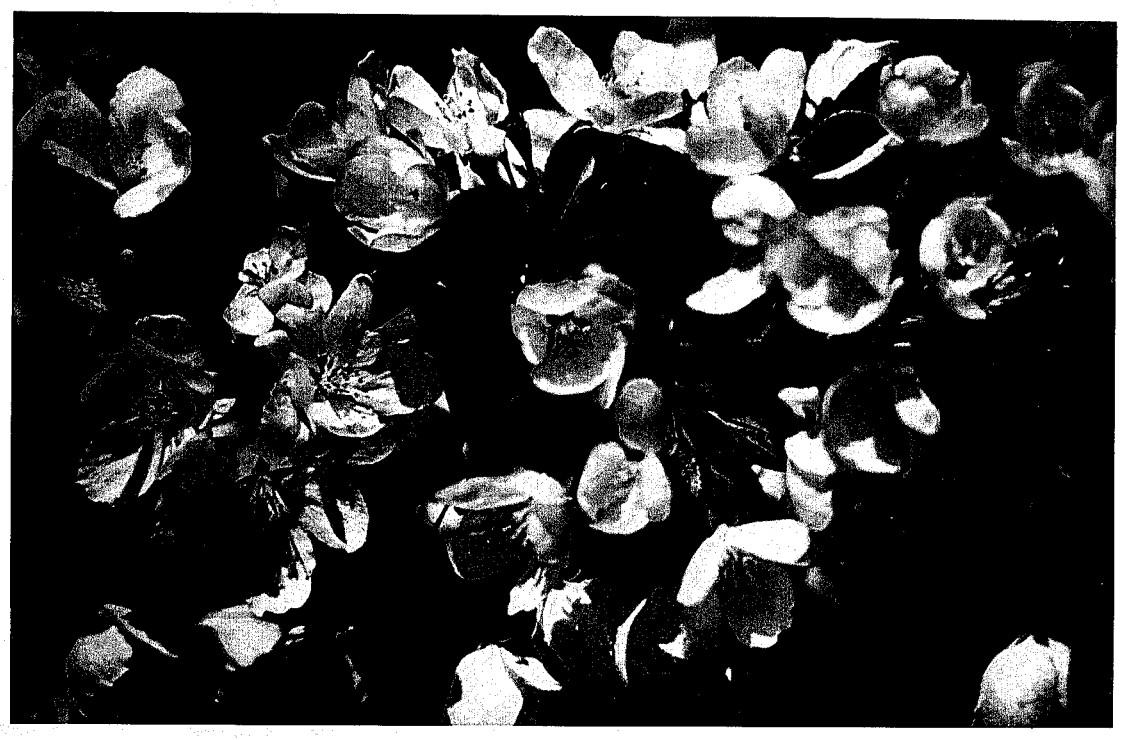

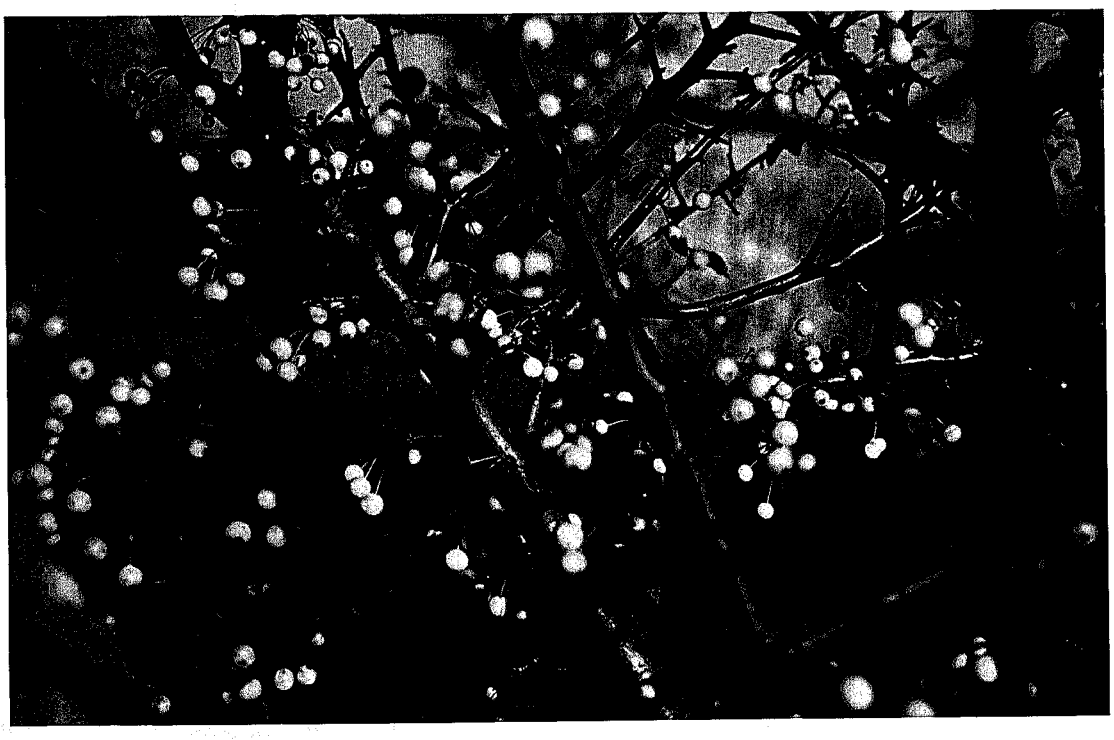

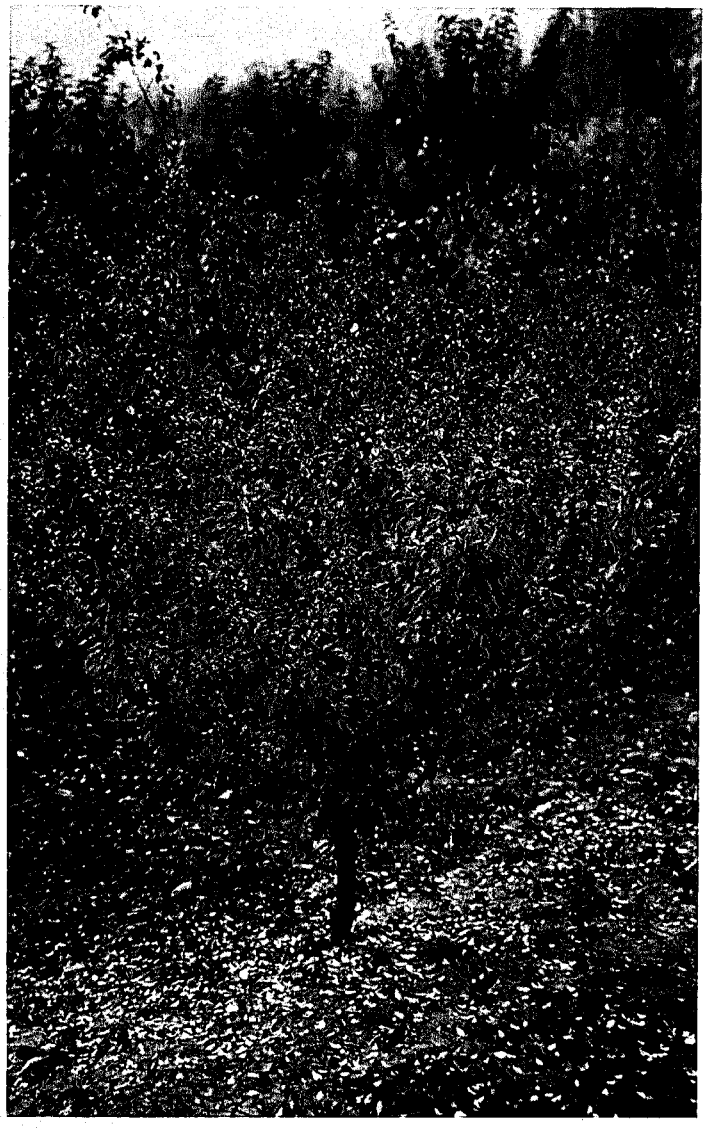

* * * * *